(12) United States Patent
Lightcap, Jr. et al.

(10) Patent No.: US 7,022,651 B1
(45) Date of Patent: Apr. 4, 2006

(54) COMPOSITION, METHOD, AND APPARATUS FOR PROTECTING PLANTS FROM INJURY CAUSED BY FROST OR FREEZING TEMPERATURES

(76) Inventors: Donald V. Lightcap, Jr., 3404 State Road 101, Woodburn, IN (US) 46797; Mark F. Smith, 14 Arbor Cir., No. 1425, Cincinnati, OH (US) 45255

( * ) Notice: Subject to any disclaimer, the term of this patent is extended or adjusted under 35 U.S.C. 154(b) by 0 days.

(21) Appl. No.: 09/128,753

(22) Filed: Aug. 4, 1998

Related U.S. Application Data (60) Provisional application No. 60/054,846, filed on Aug. 6, 1997.

(51) Int. Cl.
*A01N 37/00* (2006.01)
*A01N 25/00* (2006.01)

(52) U.S. Cl. ............... 504/320; 514/558; 514/560; 424/405

(58) Field of Classification Search ........... 504/350, 504/340, 320; 514/558, 560; 424/405
See application file for complete search history.

(56) References Cited

U.S. PATENT DOCUMENTS

| | | | |
|---|---|---|---|
| 3,669,896 A | 6/1972 | Butler | 253/307 |
| 3,712,802 A | 1/1973 | Grybek et al. | 271/79 |
| 3,712,803 A | 1/1973 | Grybek et al. | 71/79 |
| 3,790,395 A | 2/1974 | Eron | 106/122 |
| 3,964,689 A | 6/1976 | Horvath, Jr. | 239/318 |
| 4,086,331 A | 4/1978 | Neumann | 424/45 |
| 4,127,654 A * | 11/1978 | Inoue et al. | 424/216 |
| 4,244,731 A * | 1/1981 | Oshio et al. | 504/309 |
| 4,874,641 A | 10/1989 | Kittle | 427/244 |
| 5,137,094 A | 8/1992 | Broussard | 169/15 |
| 5,215,786 A | 6/1993 | Kittle | 427/244 |
| 5,251,398 A | 10/1993 | Balassa | 47/2 |
| 5,344,643 A * | 9/1994 | Thiel et al. | 424/70 |
| 5,433,758 A | 7/1995 | Thompson et al. | 47/58 |
| 5,500,220 A * | 3/1996 | Roe et al. | 424/410 |
| 5,580,567 A * | 12/1996 | Roberts | 424/405 |
| 5,653,054 A | 8/1997 | Savignano et al. | 47/2 |
| 5,756,081 A * | 5/1998 | Wdowik | 424/73 |
| 5,958,852 A * | 9/1999 | Yinanakopoulos et al. | 510/191 |

FOREIGN PATENT DOCUMENTS

| | | | |
|---|---|---|---|
| JP | 61204105 | * | 9/1986 |
| JP | 62091236 | * | 4/1987 |
| JP | 06080992 | * | 3/1994 |
| JP | 06264097 | * | 9/1994 |
| WO | 9601047 | * | 1/1996 |

OTHER PUBLICATIONS

Kraft's cool whip lite ingredient label.*
Edward G. Perkins, *Practical Handbook of Soybean processing and Utilization*, edited by David R. Erickson, AOCS Press, Champaign, IL. and United Soybean Board, St. Louis, MI (1995).

* cited by examiner

*Primary Examiner*—Gary Kunz
(74) *Attorney, Agent, or Firm*—Mark F. Smith; Smith Brandenburg & Novad Ltd.

(57) ABSTRACT

The present invention is directed to a composition, method, and apparatus for protecting plants from injury caused by frost or freezing temperatures by applying an insulating foam to the surface of plants. Plants are sprayed with a foam formed from a pre-emulsion concentrate comprising a vegetable oil, an emulsifier, and a forming agent. The pre-emulsion concentrate is mixed with water and aerated to form a foam. The foam is then directed onto the surfaces of the plant to be covered.

32 Claims, 5 Drawing Sheets

COMPOSITION, METHOD, AND APPARATUS FOR PROTECTING PLANTS FROM INJURY CAUSED BY FROST OR FREEZING TEMPERATURES

CROSS-REFERENCE TO RELATED APPLICATION

This application claims benefit of U.S. Provisional Application Ser. No. 60/054,846, filed Aug. 6, 1997 which is directed to a composition and method for protecting plants from injury caused by frost or freezing temperatures.

BACKGROUND OF THE INVENTION

This invention relates to a protecting plants from injury due to frost or freezing and, more particularly, to a composition, method, and apparatus for protecting plants from injury caused by frost or freezing temperatures.

When plants are exposed to freezing conditions during the growing season, temporary or permanent injury to the plants is likely to occur. Such injury is one of the leading causes of loss in the agricultural industry. It has been estimated that from 5 to 15 percent of the gross world agricultural product is lost to frost damage in one year. According to one estimate, approximately 10 billion dollars of agricultural products are lost annually to plant and crop freezing worldwide each year.

Frost sensitive plants and fruits generally cannot tolerate ice formation within their tissues and break down and become flacid and discolored as the plant begins to warm. Typically, during a light freeze when temperatures range between −2 C to 0 C (29 F/32 F), tender plants are often killed or damage with little effect on other vegetation. During a moderate freeze when temperatures range between −8 C and −2 C (25 F to 28 F), heavy damage will occur to most plants, including fruit blossoms and tender semi-hardy plants. During a severe freeze when temperatures drop below −9 C (24 F), heavy damage will occur to most plants.

Present methods of protecting vegetation from frost include warming the air surrounding the plants using heating devices, such as smudge pots, heat blowers and canopy heaters, placed near the plants; stirring the air over the plants by use of helicopters or air blowing equipment; and covering the plants with a insulating material such as water, fogs, material tarps, and foam sheeting material. Such methods of frost protection, however, are undesirable due to their tendency to pollute as in the case of heating devices, or are relatively expensive, as in the case of utilizing wind blowing devices or helicopters, or are relatively labor intensive as in the case of utilizing tarps or foam sheeting materials. Further, such frost protection devices often achieve limited success, particularly when the ambient air temperature falls well below freezing for a substantial amount of time or during windy conditions.

In addition to such physical methods, various chemical methods have been developed and used for reducing or preventing injury to vegetation caused by frost or freezing temperatures. Such methods include applying various chemical compounds onto the plants to be protected to lower the temperature at which plant damage occurs. Such chemical methods, however, tend to be unreliable, relatively expensive, and ecologically specious.

Accordingly, a need exists for a composition, method, and apparatus of protecting plants from injury caused by frost or freezing temperatures which is relatively inexpensive, environmentally acceptable, non-toxic, ecologically sound, and is not labor intensive.

SUMMARY OF THE INVENTION

The present invention is directed to a composition and method for producing a relatively stable insulating foam, and a method and apparatus for applying the insulating foam to the surface of plants and crops for effectively hindering or reducing injury to the plants caused by frost or freezing temperatures.

In a preferred embodiment of the invention, the composition comprises a vegetable oil, and a foaming agent and/or stabilizer for producing a relatively stable insulating foam.

In another preferred embodiment of the invention, the composition comprises a vegetable oil, an emulsifier, and a foaming agent to form a pre-emulsion concentrate which can be mixed with water to form an oil-in-water emulsion which is effective for producing a relatively stable insulating foam.

In another preferred embodiment of the invention the vegetable oil is selected from the group comprising coconut oil, corn oil, cottonseed oil, palm oil, rapeseed oil, and sunflower oil.

In another preferred embodiment of the invention the vegetable oil is a soya oil.

In another preferred embodiment of the invention the vegetable oil is a crude, non-refined vegetable oil.

In another preferred embodiment of the invention the vegetable oil is a crude, non-refined soya oil.

In another preferred embodiment of the invention, the composition of the present invention comprises an alkyl alcohol ethoxylate emulsifier.

In another preferred embodiment of the invention, the composition of the present invention comprises a foam stabilizer.

In another preferred embodiment of the invention, the composition of the present invention comprises a thickener.

In another preferred embodiment of the invention, the composition of the present invention may be used as a crop adjuvant, In another preferred embodiment of the invention, the composition of the present invention comprises a plant growth regulator.

In another preferred embodiment of the invention, the composition of the present invention comprises a pesticide.

In another preferred embodiment of the invention, the foaming agent of the present invention comprises neutralized alkyl sulfate and triethanolamine.

In another preferred embodiment of the invention, the foaming agent of the present invention comprises an amine oxide.

In another preferred embodiment of the invention, the foaming agent of the present invention comprises a quaternary ammonium compound.

In another preferred embodiment of the invention, the foaming agent of the present invention comprises an alkyl oxyalkylate.

In another preferred embodiment of the invention, the foaming agent of the present invention comprises an aryl oxyalkylate.

In another preferred embodiment of the invention, the foaming agent of the present invention comprises a hydrolyzed protein.

In another preferred embodiment of the invention, the foaming agent of the present invention comprises oxyalkylates.

In another preferred embodiment of the invention, the foaming agent of the present invention comprises neutralized alkyl sulfates.

In another preferred embodiment of the invention, the foaming agent of the present invention comprises neutralized alkyl and aryl sulfonates.

In another preferred embodiment of the invention, the foam stabilizer of the present invention comprises a carboxyalkylcellulose.

In another preferred embodiment of the invention, the thickener of the present invention comprises a mucilage.

In another preferred embodiment of the invention, the growth regulator of the present invention comprises an ethylene.

In another preferred embodiment of the invention, the pesticide of the present invention comprises malathion.

In another preferred embodiment of the invention, the pesticide of the present invention comprises mineral oil.

In a preferred embodiment of the invention, the composition of the present invention comprises methylated silica polydimethylsiloxane.

In another preferred embodiment of the invention, the composition of the present invention is stored in a manner whereby the foam concentrate is stored a holding tank in flow communication with a water source.

In another preferred embodiment of the invention, the composition of the present invention is aerated by a method and apparatus to produce a foam which is sprayed or deposited onto the surface of the plant to be protected to form an insulating foam layer or blanket.

In another preferred embodiment of the invention, the method and apparatus to aerate the composition of the present invention is by means of a nozzle having means for inducing air into the composition.

In another preferred embodiment of the invention, the composition is deposited onto plants by means of a pressurized container.

A primary object of this invention, therefore, is to provide a composition, method and apparatus of preventing or reducing injury to plants caused by frost or freezing temperatures.

Another primary object of this invention is to provide a method and apparatus for spraying plants with an insulating foam.

Another primary object of this invention is to provide a pre-emulsion concentrate which is stable and does not separate during storage.

Another primary object of this invention is to provide a pre-emulsion concentrate which can be mixed with water to form an oil-in-water emulsion.

Another primary object of this invention is to provide an insulation foam for protecting plants from injury caused by frost or freezing temperatures.

Another primary object of this invention is to provide a composition for protecting plants from injury caused by frost or freezing temperatures which is non-toxic.

Another primary object of this invention is to provide a composition for protecting plants from injury caused by frost or freezing temperatures which is ecologically acceptable.

Another primary object of this invention is to provide a composition and method of protecting plants from injury caused by frost or freezing temperatures which is relative inexpensive.

Another primary object of this invention is to provide a composition and method of protecting plants from injury caused by frost or freezing temperatures which applies relatively easily and in a relatively short amount of time.

Another primary object of this invention is to provide a composition which can be used as a crop adjuvant to assist in the adhesion and spreading of growth regulators and/or pesticides.

These and other objects and advantages of the invention will be apparent from the following drawings and detailed description of the preferred embodiments.

DETAILED DESCRIPTION OF PREFERRED EMBODIMENTS

The present invention for protecting plants from injury caused by frost or freezing temperatures comprises an insulating foam effective for providing a blanket or insulating layer along the surface of the plants to be protected. The insulating foam is produced from a composition comprising a vegetable oil and a foaming agent. Preferably, the vegetable oil comprising the insulating foam is soya oil, however, other suitable vegetable oils are coconut oil, corn oil, cottonseed oil, palm oil, rapeseed oil, and sunflower oil. In addition, the vegetable oil is preferably a crude, non-refined or nonpurified oil. It should now be apparent to one skilled in the art that the use of a crude, non-refined vegetable oil as a base component will be significantly less expensive than using a refined or a purified vegetable oil. Further, crude vegetable oils, especially crude soya oil, contain tocopherol which is a natural antioxidant and functions as a preservative. This permits the foam producing composition to be stored for use without or with the use of significantly less additional preservatives. Crude vegetable oils also contain gums which improve the oil's stickability or adhesion characteristics thereby increasing the ability of the foam to cling to the plant's surfaces. In this way, the composition may also be used as an adjuvant to assist in the adhesion and spreading of growth regulators such as ethylene, and pesticides such as mineral oil and malathion.

The insulating foam is produced from a composition comprising oil and water emulsion prepared from a pre-emulsion concentrate using an emulsifier which is suitable for providing a stable oil and emulsifier composition having a relatively large percentage of vegetable oil. One problem with producing foam which is effective for providing protection for a plant from injury caused by frost or freezing temperatures is the difficulty of providing a stable oil and emulsifier composition having a relatively large percentage of vegetable oil. This is particularly true for compositions comprising crude, non-refined vegetable oils. Emulsifiers which have been found to be suitable are alkyl, aryl or glycol ethoxylate, propoxylate, butoxylate and sulfonate-based emulsifiers.

One emulsifier which has been found to be particularly effective for producing a stable pre-emulsion concentrate comprising crude, nonpurified or nonrefined soya oil comprises a 3 mole ethylene oxide adduct of C12 and C14 alcohols. In formulating the emulsifier, about 30% to about 50% by weight of C12 alcohol is first mixed with about 50% to about 70% C14 alcohol. The C12 and C14 alcohols are then ethoxylated with 3 moles of ethylene oxide to produce the desired emulsifier.

In another preferred embodiment of the invention, it was unexpectedly found that the use of a silicone compound typically used for food systems, such as a methylated silica polydimethylsiloxane, such as sold by Dow Corning under the name Anti Foam 1500, may be used to produce a stable and relatively tight foam. Such a composition may be particularly suited for use for providing an insulating foam utilizing a pressurized container or a container using a propellant such as an inert gas or air.

Foaming agents that have been found to be suitable are quaternary ammonium compounds, amine oxides, neutralized alkyl sulfates, neutralized alkyl and aryl sulfonates, hydrolyzed protein and alkyl and aryl oxyalkylates.

Foam thickeners and stabilizers such as carboxyalkylcellulose and mucilage may also be used in the composition. Emulsifying agents may be used as foam thickeners and foam stabilizers and may also be used as emulsifiers to produce a stable pre-emulsion concentrate for storage purposes as well as to produce a stable foam.

In a preferred embodiment of the present invention, the composition effective for producing a stable foam concentrate is prepared by mixing about 40% to about 90% by weight of a crude, nonpurified or nonrefined vegetable oil with about 1% to about 40% by weight of an emulsifier, and about 0.5% to about 10% sodium lauryl sulfate and about 0.5% to about 10% triethanolamine. The composition may be stored until ready to use or shipped to the ultimate customer for use.

In order to further illustrate the invention, the following specific example of a composition for preventing or hindering injury to plants caused by frost or freezing temperatures were prepared:

EXAMPLE 1

A composition for preventing or hindering injury to plants caused by frost or freezing temperatures was prepared by mixing together by agitation a crude, nonpurified or nonrefined soya oil with an emulsifier comprising a 3 mole ethylene oxide adduct of C12 and C14 alcohols in a 500 gallon mixing vessel. The following quantities were used to produce the desired composition resulting in a stable and relatively tight insulating foam:

| Material | Volume (gal) | Vol (%) | Weight (lbs) | Wt (%) |
|---|---|---|---|---|
| Crude soya oil | 400.0 | 85.0 | 3120.0 | 85.2 |
| Emulsifier | 71.0 | 15.0 | 543.2 | 14.8 |
| | 471.0 | 100.0 | 3663.2 | 100.0 |

Agitation was provided by a 3.5 Horsepower pump. The composition was pulled from the bottom of the mixing vessel, sheared and moved by the pump through a 1.5 inch diameter hose, returned through the top of the vessel to fall back into the composition remaining in the vessel. The emulsifier was added slowly through the top of the vessel over a 30 minute period during agitation. Foam was formed on top of the composition in the vessel and began to accumulate. 15 grams of methylated silica polydimethylsiloxane, sold under the name Antifoam 1500 by the Dow Corning Company was added to the composition and agitation was continued. Unexpectedly, the Antifoam 1500 resulted in a more stable and tighter foam.

The insulating foam layer or blanket for hindering or preventing injury to plants caused by frost or freezing displayed surprising characteristics. After about ten hours, the foam formed by the composition of the present invention continued to be stable and had not broken. In addition, the foam layer appeared to have caused no detrimental effects to the plants.

EXAMPLE 2

A composition for preventing or hindering injury to plants caused by frost or freezing temperatures was prepared by mixing together by agitation a crude, nonpurified or nonrefined soya oil with an emulsifier comprising a 3 mole ethylene oxide adduct of C12 and C14 alcohols. The following ratio was used for quantities to produce the desired pre-emulsion concentrate:

| Material | Weight (%) |
|---|---|
| Crude soy oil | 75.0 |
| Emulsifier | 20.0 |
| Sodium Lauryl Sulfate | 3.0 |
| Triethanolamine | 2.0 |

Agitation was provided by a lab blender (3200 rpm) at 35 degrees C. to produce 200 grams of the concentrate. The pre-emulsion concentrate was then mixed with water to produce 3% and 9% solutions which were pumped through a aerating nozzle to produce a relatively stable and tight foam. The foam was then applied to leaves of a young tomato plant to produce an insulating layer or blanket. After five hours the foam remained relatively stable and appeared to produce no harmful effects to the tomato plant.

As previously described, the composition of the present invention comprises a relatively inexpensive, environmentally acceptable, non-toxic, and ecologically sound foam which is effective for hindering or preventing plants from injury caused by frost or freezing temperatures.

Figure 1:
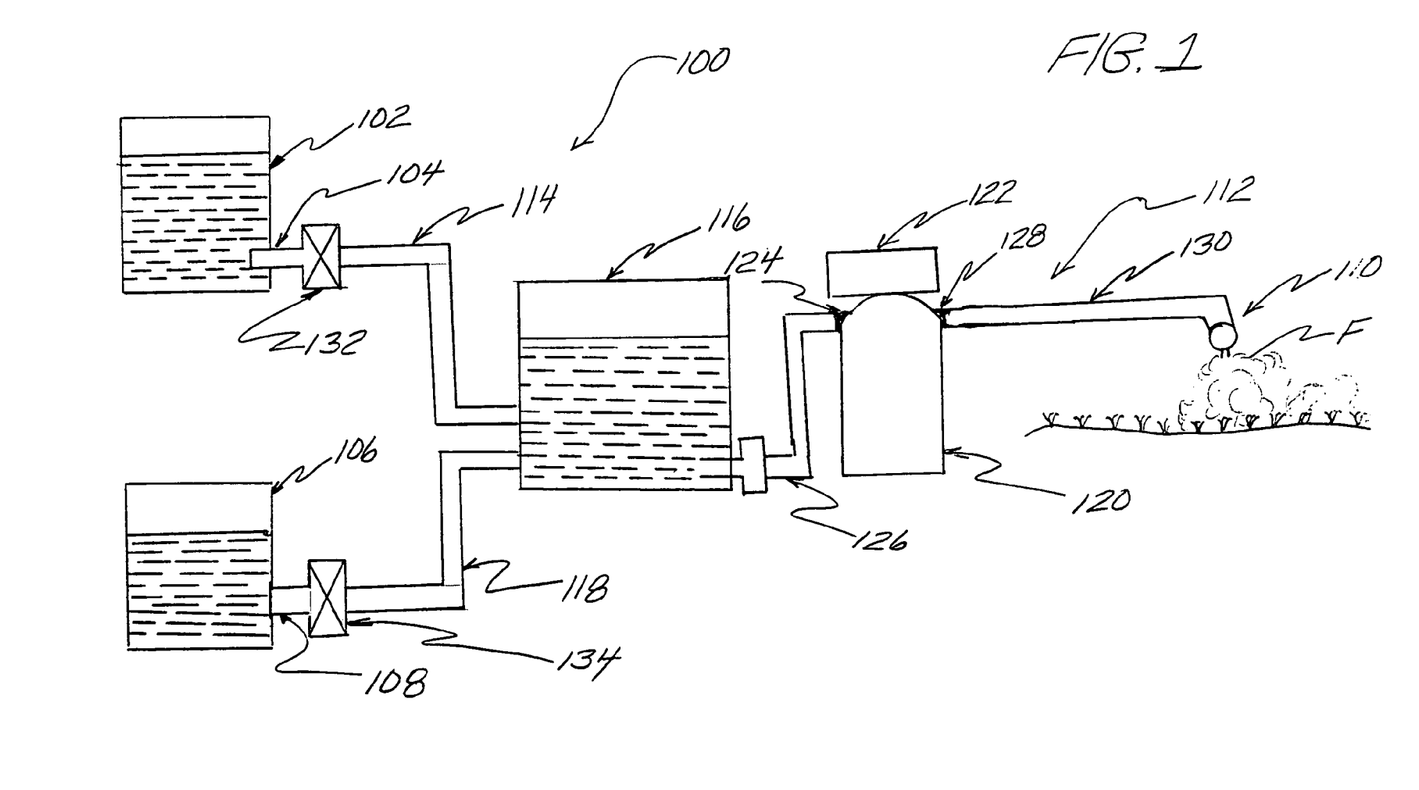
FIG. 1 is a schematic representation of a foam dispensing apparatus of the present invention showing a system for spraying and covering plants with the insulating foam of the present invention.

Referring to FIG. 1, a schematic representation of a preferred embodiment of a foam dispensing apparatus, generally designated 100, of the present invention is shown illustrating a foam dispensing system for spraying and covering plants with a blanket of insulating foam. The foam dispensing apparatus 100 comprises a pre-emulsion concentrate storage tank 102 having an outlet 104, and a water supply 106 having an outlet 108. The storage tank 102 and a conventional water supply 106 are both in fluid communication with a foam forming nozzle assembly 110 through a system of conduits, generally designated 112. In operation, the pre-emulsion concentrate of the invention is directed out of the outlet 104 of the pre-emulsion concentrate storage tank 102 and through conduit 114 to a mixer 116. Water, which has been directed to the mixer 116 from the water supply 106 through outlet 108 and conduit 118, is mixed with the pre-emulsion concentrate to form an oil and water emulsion. A fluid pump 120, powered by a conventional electric or gasoline powered motor 122, is provided to pump the oil and water emulsion to the foam forming nozzle assembly 110. It should be apparent to one skilled in the art that the pump 120 must provide sufficient pressure to blow and produced a foam spray F which can be directed onto the plants to be protected. It should also now be apparent that the required pressure is dependent on the number and size of the nozzles, the distance to blow, the length and diameter of the conduits, the coverage necessary, and the concentration of the oil and water emulsion. The pressure necessary for any particular application may be easily determined by one skilled in the art.

The pump 120 includes an inlet 124 connected to the mixer 116 through conduit 126 and an outlet 128 which is connected to the foam forming nozzle assembly 110 through conduit 130. The outlet 104 of the pre-emulsion concentrate storage tank 102 and the outlet 108 of the water supply 106 are each provided with a valves 132 and 134, respectively, for adjusting the amount of water and pre-emulsion concentrate entering the mixer 116. By adjusting the oil and water emulsion, the density of the foam can be regulated to meet the specific insulating need of the crop or plant. For example, by increasing or decreasing the ratio of the pre-emulsion concentrate and water, the density of the foam can be increased or decreased.

Figure 2:
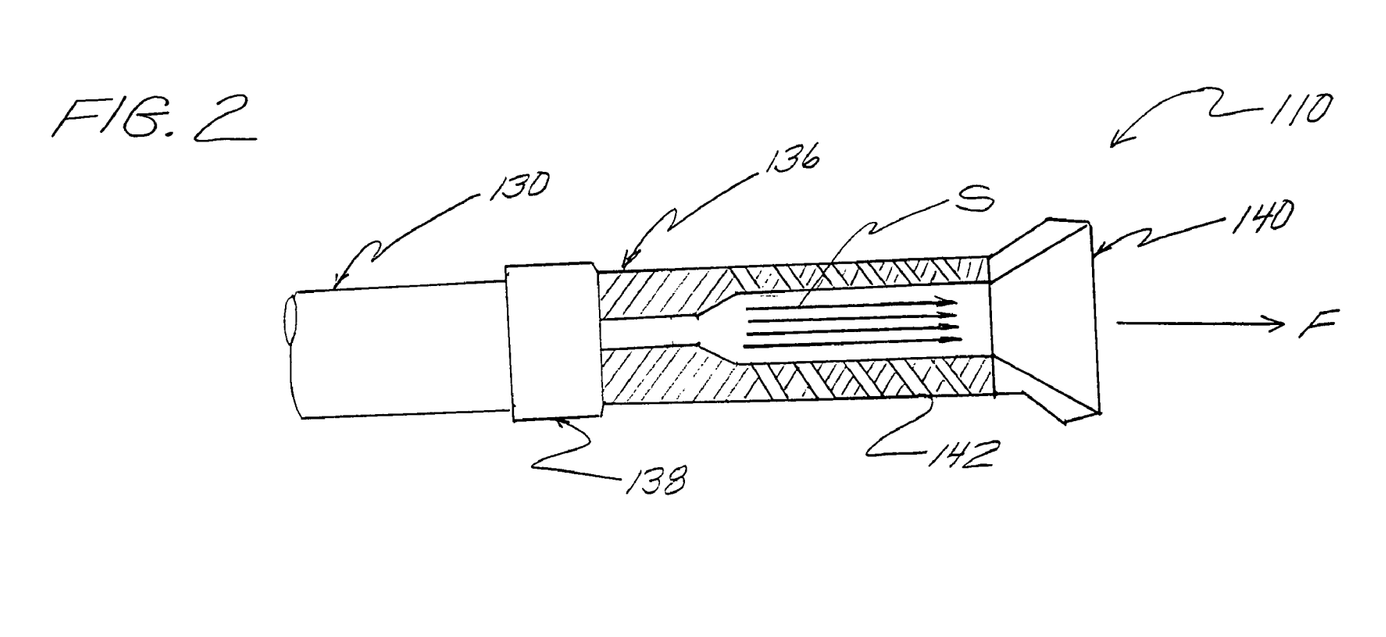
FIG. 2 is a side view, partially broken, showing in more detail the foam forming nozzle assembly of the foam dispensing apparatus of FIG. 1.

The foam forming nozzle assembly 110 for producing and spraying a foam whereby plants may be covered with an insulating blanket of foam is designed to inject or draw air into the oil and water emulsion and to direct the foam spray to the area of the plants and crops to be protected. Depending on the application, the foam forming nozzle assembly 110 may also be conventionally designed to atomize the oil and water emulsion to improve aspiration. Referring to FIG. 2, a preferred embodiment of a foam forming nozzle assembly 110 is illustrated comprising a cylindrical member 136 having an inlet 138 for receiving the oil and water emulsion through conduit 130 and an outlet 140 for discharging a foam spray F. The cylindrical member 136 is provided with a plurality of lateral air inlets 142 through which air is drawn into the oil and water emulsion stream S to form the insulating foam spray F.

Figure 3:
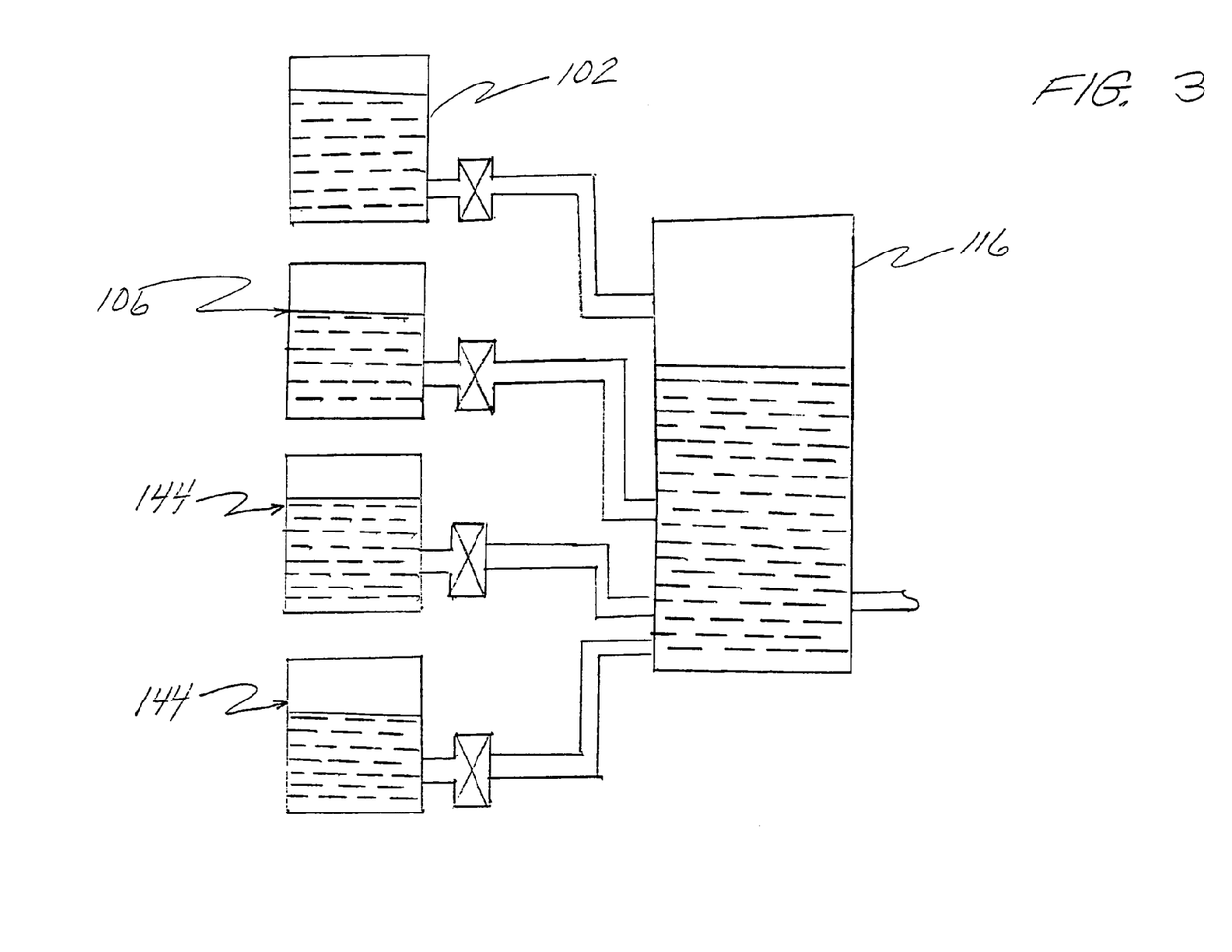
FIG. 3 is a schematic representation of another embodiment of a foam dispensing apparatus of the present invention showing another system for spraying and covering plants with the insulating foam of the present invention comprising additional supply tanks.
Figure 4:
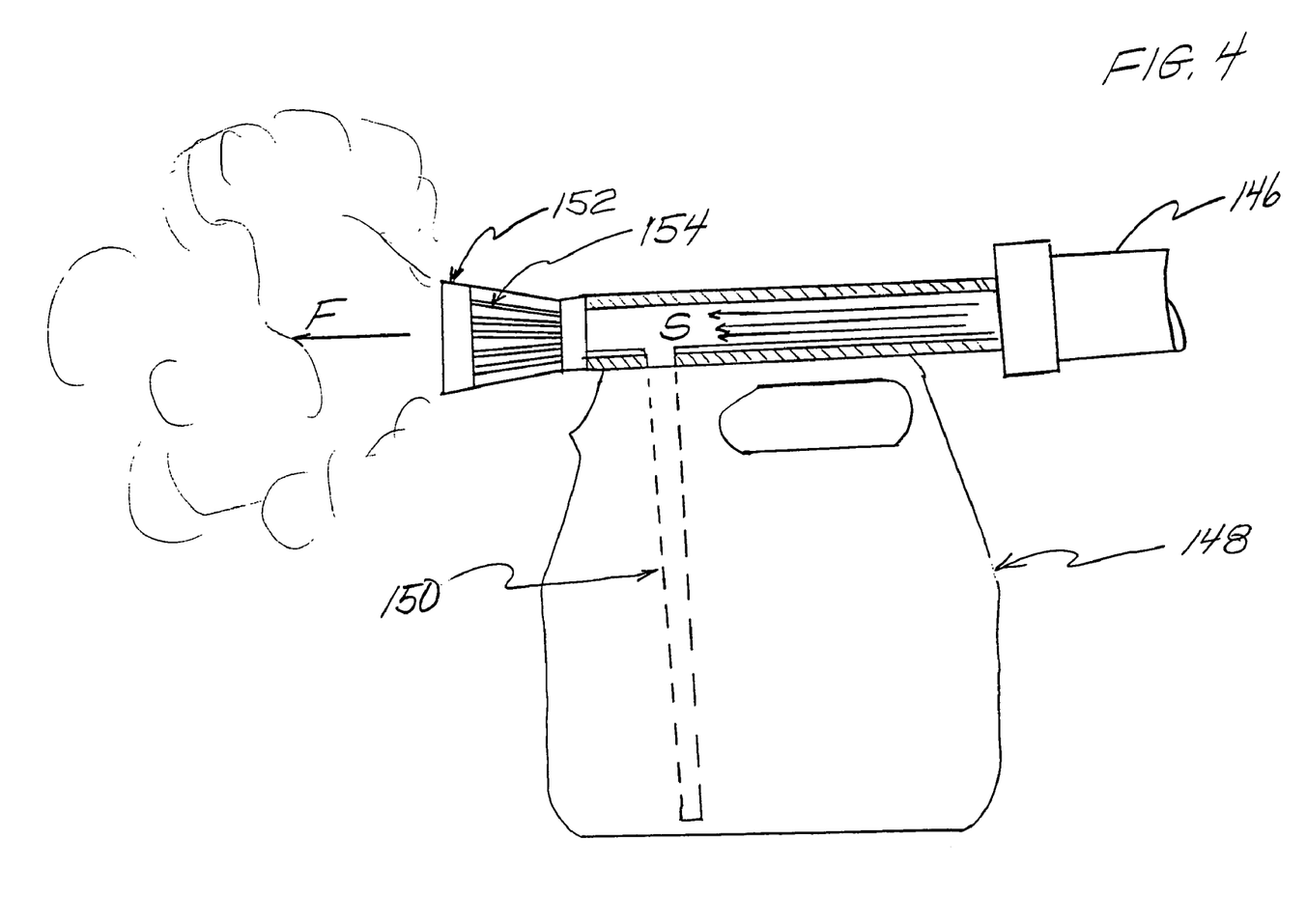
FIG. 4, is another embodiment of a foam dispensing apparatus of the present invention showing another system for spraying and covering plants with the insulating foam of the present invention having water supplied through a hose and the pre-emulsion concentrate being drawn into the water stream by aspiration or by pressure and discharged as foam through the nozzle.
Figure 5:
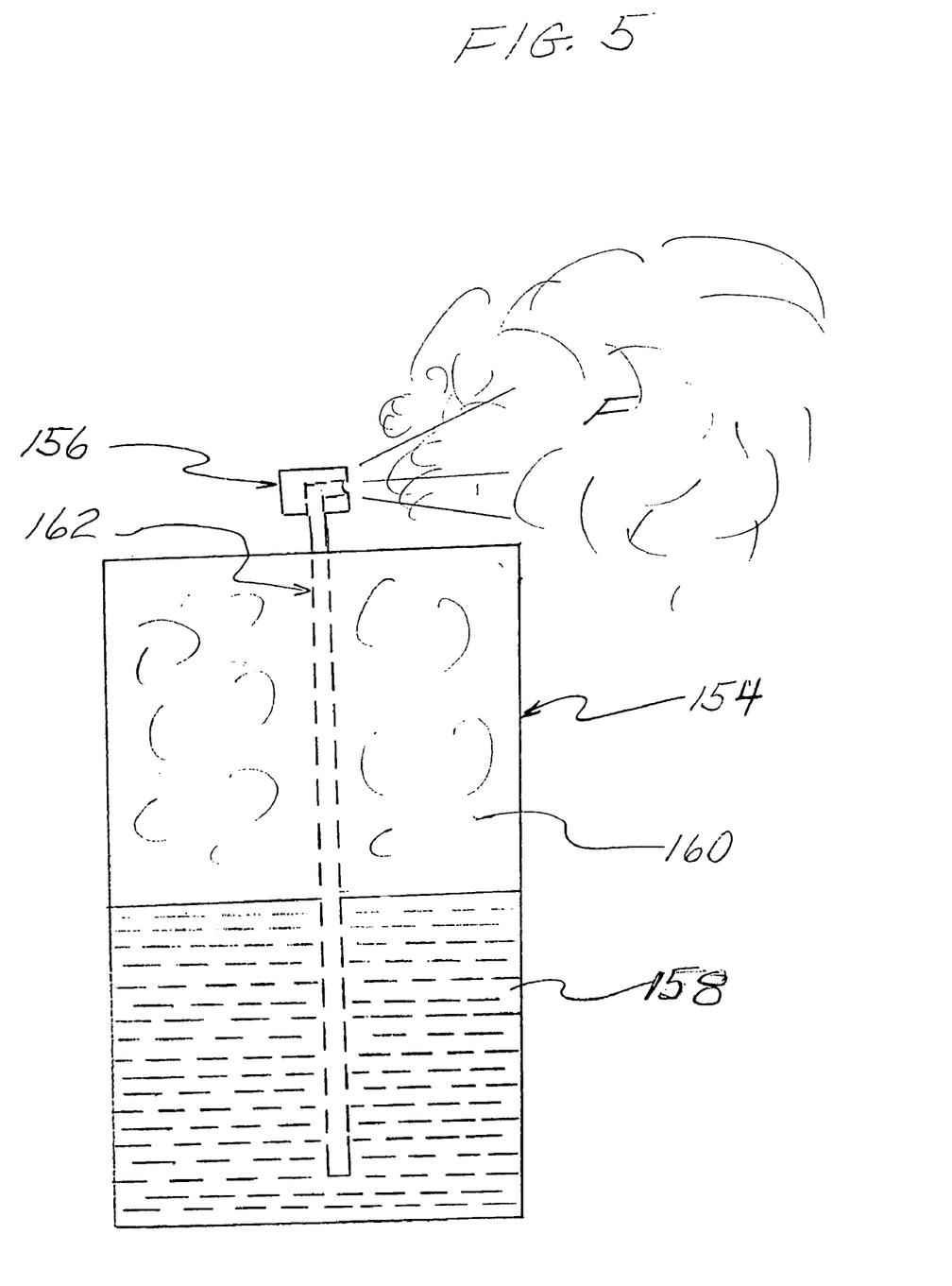
FIG. 5 is another embodiment of a foam dispensing apparatus of the present invention showing another system for spraying and covering plants having a pressurized cylinder having a spray nozzle and containing the foam concentrate of the present invention and a gas propellant.

It should be apparent to one skilled in the art that other foam dispensing apparatus using various systems may be used to form and distribute the foam of this invention across the surfaces of plants. While the foam dispensing apparatus disclosed herein illustrate and describe specific systems which may be utilized to dispense and apply foam to plants, the disclosure of such foam dispensing apparatus and systems is only an exemplification of the principals for applying a foam blanket on plants and is not intended to limit the invention to the particular foam dispensing apparatus or systems illustrated and described. For example, foam dispensing apparatus may be conventionally designed for a system which is placed within the bed of a truck or a trailer to be transported through a field. In addition, as shown in FIG. 3. the foam dispensing apparatus may include additional tanks 144 containing various types of chemicals, including herbicides, fungicides, fertilizers, insecticides and the like, to permit the foam produced by this invention to operate as a carrier. It has been found that the tacky nature of the foam produced by this invention has shown the foam to be an excellent crop adjuvant to assist in the adhesion and spreading of growth regulators and/or pesticides. Hand held systems having foam dispensing apparatus, such as shown in FIG. 4, may include hose-end dispenser devices whereby water is supplied through a hose 146 and the pre-emulsion concentrate is drawn from a holding container 148 into the water stream S through a hose 150 by aspiration or by pressure and mixed with the water stream S and discharged as foam through the nozzle 152. Another foam dispensing apparatus is shown in FIG. 5 comprising a pressurized cylinder 154 and a spray nozzle 156. Contained within the pressurized cylinder 154 is the foam concentrate of the present invention 158, such as previously shown in Example 1, and a gas propellant 160 for expelling the concentrate out through conduit 162 and spray nozzle 156 which forms the insulating foam F.

It should also now be apparent to one skilled in the art that the systems using foam producing apparatus, such as previously described, may include the use of a plurality of foam producing nozzles or require such nozzles to be mounted on various devices such as poles, booms, elongated manifolds and the like to permit effective plant coverage.

It should also now be apparent to one skilled in the art that the foam dispensing apparatus can easily be incorporated into existing or conventional crop spraying systems which are supplied with or may be equipped with air aspiration nozzles.

There has thus been provided a novel composition and method for producing a relatively stable insulating foam and an apparatus and a method of applying the insulating foam to the surface of plants and crops for effectively hindering or reducing injury to plants and crops caused by frost or freezing temperatures. The composition of the present invention is relatively inexpensive, environmentally acceptable, ecologically sound, nontoxic, and should have no detrimental effects on plant life or development. In fact, it has been found that the use of the vegetable oil of the present invention operates effectively as a pesticide to reduce insect damage. It has also been found that the tacky nature of the foam produced by this invention allows the foam to be used as a crop adjuvant.

Although this invention has been shown and described with respect to detailed embodiments thereof, it will be understood by those skilled in the art that various changes in form and detail thereof may be made without departing from the basic principles, spirit, and scope of the claimed invention.

We claim:

1. An agricultural composition for producing a foam for use in protecting plants against frost or freezing temperatures consisting essentially of:
   about 40% to about 90% by weight of vegetable oil;
   an emulsifier; and
   a foaming agent;
   wherein said vegetable oil is selected from the group consisting of coconut oil, corn oil, cottonseed oil, palm oil, rapeseed oil, soya oil, and sunflower oil.

2. The composition of claim 1 wherein the composition is incorporated into water.

3. The composition of claim 1 wherein said vegetable oil is a crude vegetable oil.

4. The composition of claim 3 wherein said emulsifier is a compound of silicone.

5. The composition of claim 4 wherein said compound of silicone is a methylated silica polydimethylsiloxane.

6. The composition of claim 1 wherein said emulsifier is an alkyl oxyalkylate.

7. The composition of claim 1 wherein said foaming agent are neutralized alkyl sulfates.

8. The composition of claim 1 wherein said foaming agent are neutralized alkyl sulfonates.

9. The composition of claim 1 wherein said foaming agent are neutralized aryl sulfonates.

10. The composition of claim 1 wherein said foaming agent are neutralized alkyl sulfate and triethanolamine.

11. The composition of claim 1 wherein said foaming agent is an amine oxide.

12. The composition of claim 1 wherein said foaming agent is a quaternary ammonium compound.

13. The composition of claim 1 wherein said foaming agent is an aryl oxyalkylate.

14. The composition of claim 1 wherein said foaming agent is a hydrolyzed protein.

15. The composition of claim 1 wherein said foaming agent are oxyalkylates.

16. A composition for producing a foam for use in protecting plants against frost or freezing temperatures consisting essentially of:
   a pre-emulsion concentrate made up of about 40% to about 90% vegetable oil, an emulsifier, and a foaming agent;
   water; and
   one or more components selected from the group consisting of a foam stabilizer, a foam thickener, sodium lauryl sulfate and triethanolamine;
   wherein said vegetable oil is selected from the group consisting of soya oil, coconut oil, corn oil, cottonseed oil, palm oil, rapeseed oil, and sunflower oil;
   wherein said emulsifier is selected from the group consisting of alkyl, aryl, or glycol ethoxylate, propoxylate, butoxylate or sulfonate based emulsifiers; and
   wherein said foaming agent is selected from the group consisting of quaternary ammonium compounds, amine oxides, neutralized alkyl sulfates, neutralized alkyl and aryl sulfonates, hydrolyzed protein, and oxyalkylates.

17. The composition of claim 16 wherein said emulsifier comprises a 3 mole ethylene oxide adduct of C12 and C14 alcohols.

18. The composition of claim 16 wherein said emulsifier comprises about 30% to about 50% by weight of C12 alcohol and about 50% to about 70% C14 alcohol and wherein said C12 alcohol and said C14 alcohol are ethoxylated with 3 moles of ethylene oxide.

19. The composition of claim 16 wherein said foam stabilizer and thickener is carboxyalkylcellulose and mucilage.

20. The composition of claim 16 wherein said vegetable oil is a crude vegetable oil.

21. The composition of claim 16 wherein said pre-emulsion concentrate is formed from about 75% by weight of soya oil; about 20% by weight of said emulsifier comprising 3 mole ethylene oxide adduct of C12 alcohol and C14 alcohol; about 3% by weight of sodium lauryl sulfate; and about 2% by weight of triethanolamine.

22. A method of protecting plants from frost or freezing temperatures comprising the steps of:
   producing a pre-emulsion concentrate comprising a vegetable oil, an emulsifier and a foaming agent;
   mixing the pre-emulsion concentrate with water to form an oil and water emulsion;
   aerating the oil and water emulsion to form a foam; and
   applying the foam to the plants.

23. The method of claim 22, wherein the vegetable oil is a crude vegetable oil.

24. The method of claim 22, wherein the emulsifier is selected from the group consisting of alkyl, aryl, or glycol ethoxylate, propoxylate, butoxylate, and sulfonate based emulsifiers.

25. The method of claim 22, wherein the foaming agent is selected from the group consisting of neutralized aryl sulfonates, neutralized alkyl sulfate and triethanolamine, aryl alcohol, hydrolyzed protein, and oxyalkylates.

26. The method of claim 22, wherein the emulsion includes a foam stabilizer.

27. The method of claim 22, wherein the emulsion includes a plant growth regulator.

28. The method of claim 22, wherein the emulsion includes a pesticide.

29. A method of spraying plants comprising the steps of:
   producing a pre-emulsion concentrate consisting essentially of about 40% to about 90% by weight of vegetable oil and an emulsifier selected from the group consisting of alkyl, aryl, or glycol ethoxylate, propoxylate, butoxylate, and sulfonate based emulsifiers;
   mixing the pre-emulsion concentrate with water to form an oil and water emulsion; and
   applying the oil and water emulsion onto the surfaces of the plants.

30. A method of treating plants comprising the steps of:
   producing a pesticide consisting essentially of about 40% to about 90% by weight of vegetable oil and an emulsifier; and
   placing the pesticide into water and applying the water and the pesticide to the surface of the plants;
   wherein said vegetable oil is selected from the group consisting of coconut oil, cottonseed oil, palm oil, rapeseed oil, soya oil, and sunflower oil.

31. The method of claim 30, wherein the vegetable oil is a crude vegetable oil.

32. The method of claim 30, wherein the emulsifier is selected from the group consisting of alkyl, aryl, or glycol ethoxylate, propoxylate, butoxylate, and sulfonate based emulsifiers.

* * * * *